US007015462B2

(12) United States Patent
Karas

(10) Patent No.: US 7,015,462 B2
(45) Date of Patent: Mar. 21, 2006

(54) SEPARATION OF COMPONENTS OF AN ANALYSIS SAMPLE IN AN ION MOBILITY SPECTROMETER USING A SUPPLY OF SELECTIVELY INTERACTIVE GASEOUS PARTICLES

(76) Inventor: Michael Karas, Falkensteinstr.9, 65795 Hattersheim (DE)

( * ) Notice: Subject to any disclaimer, the term of this patent is extended or adjusted under 35 U.S.C. 154(b) by 67 days.

(21) Appl. No.: 10/479,137

(22) PCT Filed: May 28, 2002

(86) PCT No.: PCT/DE02/01963

§ 371 (c)(1),
(2), (4) Date: May 11, 2004

(87) PCT Pub. No.: WO02/096805

PCT Pub. Date: Dec. 5, 2002

(65) Prior Publication Data

US 2004/0178340 A1 Sep. 16, 2004

(30) Foreign Application Priority Data

May 28, 2001 (DE) ................................ 101 25 907

(51) Int. Cl.
*H01J 49/40* (2006.01)
*G01N 27/64* (2006.01)

(52) U.S. Cl. ..................................... 250/287; 250/282

(58) Field of Classification Search ...................... None
See application file for complete search history.

(56) References Cited

U.S. PATENT DOCUMENTS

| 4,551,624 A | | 11/1985 | Spangler et al. |
| 4,960,762 A | | 10/1990 | Sellergren et al. |
| 5,095,206 A | * | 3/1992 | Bacon et al. ............... 250/282 |

(Continued)

FOREIGN PATENT DOCUMENTS

| DE | 693 12 471 T2 | 7/1997 |
| DE | 197 26 152 A1 | 12/1998 |
| EP | 0219 602 A2 | 4/1987 |
| EP | 0 509 171 A1 | 10/1992 |
| WO | WO 00/01642 | 1/2000 |
| WO | WO 00/08454 | 2/2000 |
| WO | WO 00/64572 | 11/2000 |

OTHER PUBLICATIONS

Ota Hiromichi et al., Patent Abstracts of Japan, "Production of Sulfur-containing Optically Active Alcohol", Publication No. 09191892, Publication Date: Jul. 29, 1997.

(Continued)

Primary Examiner—Jack I. Berman

(57) ABSTRACT

A process for separation of components of a sample in an ion mobility spectrometer using a supply of selectively interactive gaseous particles. The components to be separated carry out selective interaction processes in a drift tube of the ion mobility spectrometer with specifically selected particles, in particular enantiometric collision molecules, which are supplied to a gas inlet, in such a way that they exhibit different rates of mobility during their drift from a sample inlet through the drift tube to an ion collector. This enables the ions to be detected in the ion collector in a time-delayed manner.

17 Claims, 4 Drawing Sheets

U.S. PATENT DOCUMENTS

| | | | |
|---|---|---|---|
| 5,234,838 | A | 8/1993 | Bacon, Jr. |
| 5,306,561 | A | 4/1994 | Frechet et al. |
| 6,225,623 | B1 | 5/2001 | Turner et al. |
| 6,372,932 | B1 | 4/2002 | Kepert et al. |
| 6,639,212 | B1 * | 10/2003 | Guevremont et al. ....... 250/282 |
| 6,639,214 | B1 * | 10/2003 | Ketkar et al. ............... 250/287 |

OTHER PUBLICATIONS

Yansheng Liu et al., Characterizing Oligosaccharides Using Injected-Ion Mobility/Mass Spectrometry, Analytical Chemistry, vol. 69, No. 13, Jul. 1, 1997, pp. 2504-2509.

Ching Wu et al, "Electrospray Ionization High-Resolution Ion Mobility Spectrometry—Mass Spectrometry", Analytical Chemistry, vol. 70, No. 23, Dec. 1998, pp. 4929-4938.

G. Reid Asbury et al., "Using Different Drift Gases to Change Separation Factors ($\alpha$) in Ion Mobility Spectrometry", Analytical Chemistry, vol. 72, No. 3, Feb. 2000, pp. 580-584.

Mitch Jacoby, "Fast Separations for Chiral Drugs", C&EN Chicago, Science & Technology, May 2001, vol. 79, No. 21, pp. 68-69.

D. Scarcella et al., "Optimization of a simple method for the chiral separation of phenethylamines . . . ", Forensic Science International, vol. 89, May 1997, pp. 33-46.

Yansheng Liu et al, "Characterizing Oligosaccharides Using Injected-Ion Mobility/Mass Spectrometry", Analytical Chemistry, vol. 69, No. 13, Jul. 1997, pp. 2504-2509.

Cherokee S. Hoaglund et al., "Three-Dimensional Ion Mobility/TOFMS Analysis of Electrosprayed Biomolecules", Analytical Chemistry, vol. 70, No. 11, June 1998, pp. 2236-2242.

\* cited by examiner

Fluoxetine

Drift time (μs)

SEPARATION OF COMPONENTS OF AN ANALYSIS SAMPLE IN AN ION MOBILITY SPECTROMETER USING A SUPPLY OF SELECTIVELY INTERACTIVE GASEOUS PARTICLES

DESCRIPTION

Separation of components of a sample in an ion mobility spectrometer using a supply of selectively interactive gaseous particles The present invention relates to a separation process and to an ion mobility spectrometer for separating components present in a sample, in particular chiral components.

A compound is referred to as chiral when it cannot be made to cover a compound having the mirror-image structure. Many chemical compounds are chiral and can occur in two forms which are referred to as enantiomers. The two enantiomeric compounds have different optical activity, one enantiomeric form being composed of levorotatory molecules, while the other, enantiomeric form is composed of the dextrorotatory molecules having the corresponding structure. Usually, the two enantiomeric compounds are present as what is known as a racemic mixture or racemate which is composed of the same proportions of each of the enantiomeric forms.

Enantiomericity is therefore a special case of stereoisomericity. Enantiomers are stereoisomers of a molecule which behave toward each other like an image and mirror image. All of their physical properties correspond, except the direction in which they rotate the plane of vibration of linear-polarized light, i.e. they differ in a specific optical activity. Further, all of their chemical properties correspond, except the reactivity toward other chiral compounds (Lexikon der Biochemie und Molekularbiologie [Dictionary of Biochemistry and Molecular Biology], Verlag Herder, Freiburg in Breisgau, 1991, ISBN 3-451-22064-4). This fact is extremely significant in the biochemical field, since all natural proteins contain chiral amino acids and have chiral centers. For example, the particular interest of the pharmaceutical industry lies herein in analytical processes for detecting and for separating enantiomers in the development of novel chemical preparations and active ingredients.

The biochemical actions of two enantiomeric compounds often differ very markedly. As a result of the chiral amino acids in the peptides and proteins, the chirality of a chemical preparation is decisive for its physiological and medicinal action. The pharmaceutical industry and other branches of industry such as crop protection are therefore reliant upon high-performance processes for preparing enantiomerically pure substances. The demand for chiral synthetic building blocks for the preparation of drugs, crop protection agents or aromas has been rising steadily for some time. As a consequence, commercially practicable production processes and analysis processes for enantiomerically pure compounds have experienced rapid development in the last few years.

The processes which are employed for these purposes or otherwise known in the prior art are diverse. An important analysis process is liquid or gas chromatography. In this process, the analysis mixture is mixed with an externally prepared carrier medium and separated in a separating column as a function of the different mobility of the molecules, and the individual components passing in succession through the chromatography column as a function of their different retention times are detected by means of a suitable detector. To separate the enantiomers in gas chromatography, separating columns are required which are coated with suitable chiral compounds. One or the other form of the molecules to be separated forms intermediate associations of differing stability with the stationary phase, which leads to different run times in the separating column. This process, having an elution time of 20–30 minutes for one sample, is relatively time-consuming. A further disadvantage of this process is that the enantiomeric molecules can often have very similar retention times.

It is also known that that ion mobility spectrometry (IMS) can be used to separate and to detect chemical substances. This technique typically also requires a carrier gas medium in addition to the analysis gas. The analysis gas is ionized in an ionization apparatus and subsequently drifts in a carrier gas medium in an electrical field along a drift zone, and the different gas ions separate in accordance with their different ion mobility. An ion collector at the end of the drift zone detects the ions, arriving offset in time, of the different gas ions. A high-resolution ion mobility spectrometer which is directly connected to the ionization apparatus is described, for example, in the publication of Wu, W. F. Siems, G. R. Asbury and H. H. Hill Jr. In Anal. Chem., 1998, 70, 4929–4938 ("Wu").

In the publication of G. Asbury, H. H. Hill in Anal. Chem., 2000, 72, 580–584 ("Asbury"), it has been shown that ion mobility spectrometry can be used under certain adjustable conditions such as pressure and temperature to separate isomers from amino acids such as leucine and isoleucine, which is not possible directly with mass spectrometry as a consequence of the equal molecular weight. In the separation of the isomers, the different molecular size is utilized, which has the consequence of different ion mobility in the inert carrier gas. However, how enantiomeric components can be separated from each other in an ion mobility spectrometer does not become evident from this publication.

The article published on May 21, 2001, "Fast Separations for Chiral Drugs" by Mitch Jacoby in the journal Chemical and Engineering News of the American Chemical Society describes a process, developed by Prof. Cooks at Purdue University, for separating chiral components in a mass spectrometer. In this process, cluster ions are initially formed, each of which contain a copper$^{2+}$ ion, the molecule to be analyzed in one of the two enantiomeric forms and two molecules of a chiral reference compound (L-tyrosine), which are separated in a first stage of a mass spectrometer. These cluster ions are excited energetically and subsequently decompose, and the daughter ions containing the enantiomeric components differ slightly in their energy and lead to fragments which differ in their intensity ratios. The fragment ions are detected separately in a second stage of the mass spectrometer. Although this process enables relatively rapid detection, it is reliant on the use of relatively expensive tandem mass spectrometers or mass spectrometers which allow multiple separation steps.

In the case of other compounds which are nonchiral but very similar to each other, for example very similar proteins, one problem is to be able to separate them in an ion mobility spectrometer in a conventional manner reliably, with high process speed and with reasonable design requirements for the apparatus.

It is therefore an object of the present invention to specify a separation process and a corresponding apparatus for the separation of components present in a sample, in particular chiral components, by which the separation can be carried out with high separating performance under reasonable design requirements for the apparatus.

This object is achieved by the features of the independent patent claims. Advantageous embodiments of the process and further developments of the apparatus are specified in the subclaims.

The present invention is illustrated hereinbelow with reference to the separation of chiral components. However, the invention is equally applicable to nonchiral components which are present in a sample.

In a conventional ion mobility spectrometer, the chiral components present in an analysis sample supplied can in principle not be separated from each other, since the enantiomeric molecules are subject to identical interactions with the inert gas molecules. As a consequence of identical molecular size, molecular mass and lack of steric selectivity of the drift gas with respect to the symmetry differences of the two enantiomeric forms of the molecules of the analysis gas supplied, there are no differences in the mobilities or drift times. The invention is based on the essential concept of generating a state in the drift chamber in which the chiral components, as they drift from the sample inlet through the drift chamber to an ion collector, have different mobilities, so that peaks offset in time can be detected at the ion collector.

For this purpose, not only are the sample and the inert carrier gas supplied to the ion mobility spectrometer, but also what is known as a separating substance which contains particles which interact selectively with the molecules of the chiral components of the sample supplied. Interactions take place between the chiral molecules and the particles of the separating substance.

In a first embodiment of the process according to the invention, the separating substance may be what is known as a collision medium, in particular a collision gas, in which collision molecules are present which enter into collision processes having certain collisional cross sections with the molecules of the chiral components to be separated. In this embodiment, the gaseous particles according to the invention are thus formed by molecules. It is known from molecular physics that the collisional cross sections depend upon the nature of the interactive forces determining the collision process. The interactive forces may be, for example, weak van der Waals forces or strong ion-dipole interactions. The ions may also enter into short-lived metastable compounds and clusters with the neutral molecules.

The strength of the interactions with the collision molecules determines the retention time of the enantiomeric molecule ions. When one of the enantiomeric molecules, i.e. one chiral component, has a stronger interaction with the neutral collision molecules than the other, its retention time is thus extended in comparison to the other chiral component. It therefore has to be the aim to select a collision molecule which interacts preferentially with one of the two enantiomers, but enters into minor interactions with the particular other enantiomer. The interactions of the collision molecules with the enantiomers should thus have different collisional cross sections. From a number of collision molecules which may be known and can be used in principle, preference is given to selecting that which gives the largest difference in the collisional cross sections in collision processes with the enantiomeric forms. The high-interaction enantiomer thus has a comparatively prolonged retention time, so that two peaks separated in time for the arrival of the enantiomers can be measured at the ion detector.

The collision medium selected is preferably a reactive gas which essentially enters neither into charge transfer processes nor chemical reactions with the enantiomers, but brings about energy exchange in the event of gas collisions, which is dependent upon the enantiomeric form of the analyte gas molecule.

The selectively interactive collision molecules may, for example, be molecules which are an enantiomeric constituent of a chiral substance. Such molecules may act as receptor molecules which interact preferentially with a chiral component of the sample without bringing about chemical reactions or charge transfer (such molecules are sometimes also referred to as APCA molecules (antipodal chiral agents)). The collision medium used may thus be a gas which contains such collision molecules. In an exemplary embodiment which is illustrated further down, a racemic mixture of fluoxetine is separated into its enantiomeric constituents by adding S-2-butanol collision molecules, preferably as a collision gas, to the drift chamber. As will be explained, a carrier gas, preferably an inert gas such as $N_2$, is also supplied to the drift chamber. The ratio of collision medium or gas to carrier gas may be as desired, and the carrier gas may in principle even be omitted, or its function may be assumed by the collision medium/collision gas.

However, the collision molecules may also be other molecules which are not enantiomeric constituents of a chiral compound. However, their mode of action will be restricted to magnifying differences already present in the mobility of molecules of a sample to be separated in inert drift gases, i.e. to distinctly improve the analytical separating performance compared to an ion mobility spectrometer of known type and operation ("conventional").

In a second embodiment, the separating substance may be such that the selectively interactive gaseous particles present therein in accordance with the invention may be macroscopic particles, for instance macromolecules or nanoparticles, which may likewise enter into selective interaction processes with the molecules of the components to be separated. These may be, for example, the bucky-ball-shaped fullerene or $C_{60}$ molecules known per se, on whose surfaces the two enantiomeric components may be bound in interaction processes for different periods. The nanotubes (which may, for example, likewise consist substantially of carbon) which are likewise known may also be included, which are tunneled through by the two enantiomeric forms in different periods.

Also conceivable are different mixed forms between the collision molecules mentioned in the first embodiment and the macroscopic particles of the second embodiment. For example, the separating substance may contain the particles already described of the second embodiment, to whose surfaces collision molecules of the first embodiment are bound.

In the specialist world there exist more or less clear definitive concepts of what an ion mobility spectrometer refers to and what is to be encompassed by it. Unbound from such definitive limitations in specialist circles, the term ion mobility spectrometer in this application is subject to its own definition. When this application refers to an ion mobility spectrometer, this means a drift space in its most general sense, in particular a drift chamber, in which ionized molecules pass through a drift zone under the influence of an electrical field. Such an ion mobility spectrometer thus does not necessarily include an ionization unit attached thereto, although it is advantageously and practically usually present and connected securely to the drift chamber. This does not exclude the possibility that an ion mobility spectrometer, as in the exemplary embodiments described below, is regarded as an object which includes further units such as an ionization unit.

The ionization technique used is preferably a technique which functions at atmospheric pressure or higher pressure, for example electrospray ionization or MALDI. The ionization source is preferably connected directly to the drift tube of the high-resolution ion mobility spectrometer. It is possible to use an ion mobility spectrometer as has been described, for example in the publication "Wu" mentioned at the outset.

An ion mobility spectrometer according to the invention for the separation of chiral components present in a sample has a drift chamber, a sample inlet and a separating substance inlet for the introduction of at least one separating substance in which particles are present which selectively interact with the molecules of the chiral components.

Typically, a carrier gas or drift gas is supplied to the ion mobility spectrometer and is usually an inert gas, for example $N_2$. For this purpose, the ion mobility spectrometer according to the invention may also have a carrier gas inlet in a manner known per se. While, for example, the sample inlet is disposed at one end of the drift tube, the carrier gas inlet is usually disposed at the opposite end. The drift tube may therefore be provided with a total of three gas inlets for the sample, the collision gas and the carrier gas. However, in an advantageous embodiment, a common gas inlet is provided for the supply of the separating substance and of the carrier gas, in which case separating substance and carrier gas are mixed in the gas supply system connected to the common gas inlet. The sample inlet is thus disposed at one end of the drift tube, while the common gas inlet for separating substance and carrier gas is disposed at the opposite end of the drift tube.

The sample inlet, the carrier gas inlet and the separating substance inlet may also be combined to form a single inlet orifice.

The process according to the invention can be carried out in such a way that the separating substance is a collision medium containing collision molecules as described above, for instance a collision gas, and that an inert drift or carrier gas is used which is known to be "doped" with a relatively small amount of the collision gas. The relative proportion of the collision gas may, for example, as in the exemplary embodiment shown below, be approx. 5 mol %. However, the relative proportion may in principle also assume any other intermediate value between 0 and 100 mol %. It is therefore also conceivable in theory that the collision gas also assumes the function of the drift gas, without an inert drift gas being present.

The ion mobility spectrometer according to the invention may be coupled to other units in various ways. It is possible, for example, to connect a mass spectrometer or another ion collection unit to the outlet of the ion mobility spectrometer, in order to carry out quantitative analysis of the masses of the enantiomers. It is also possible to dispose a chromatographic or electrophoretic unit upstream of the ion mobility spectrometer and to connect it to its inlet, in order to further increase the separating performance of the apparatus.

However, the great advantage of the process according to the invention is that it in principle dispenses with the costly and compound-selective chromatographic systems and enables inexpensive and simultaneously rapid identification of enantiomeric molecules. The separation of the chiral components of a sample can be carried out in a few milliseconds.

The invention is illustrated in detail hereinbelow with reference to exemplary embodiments in conjunction with the drawings.

Figure 1:
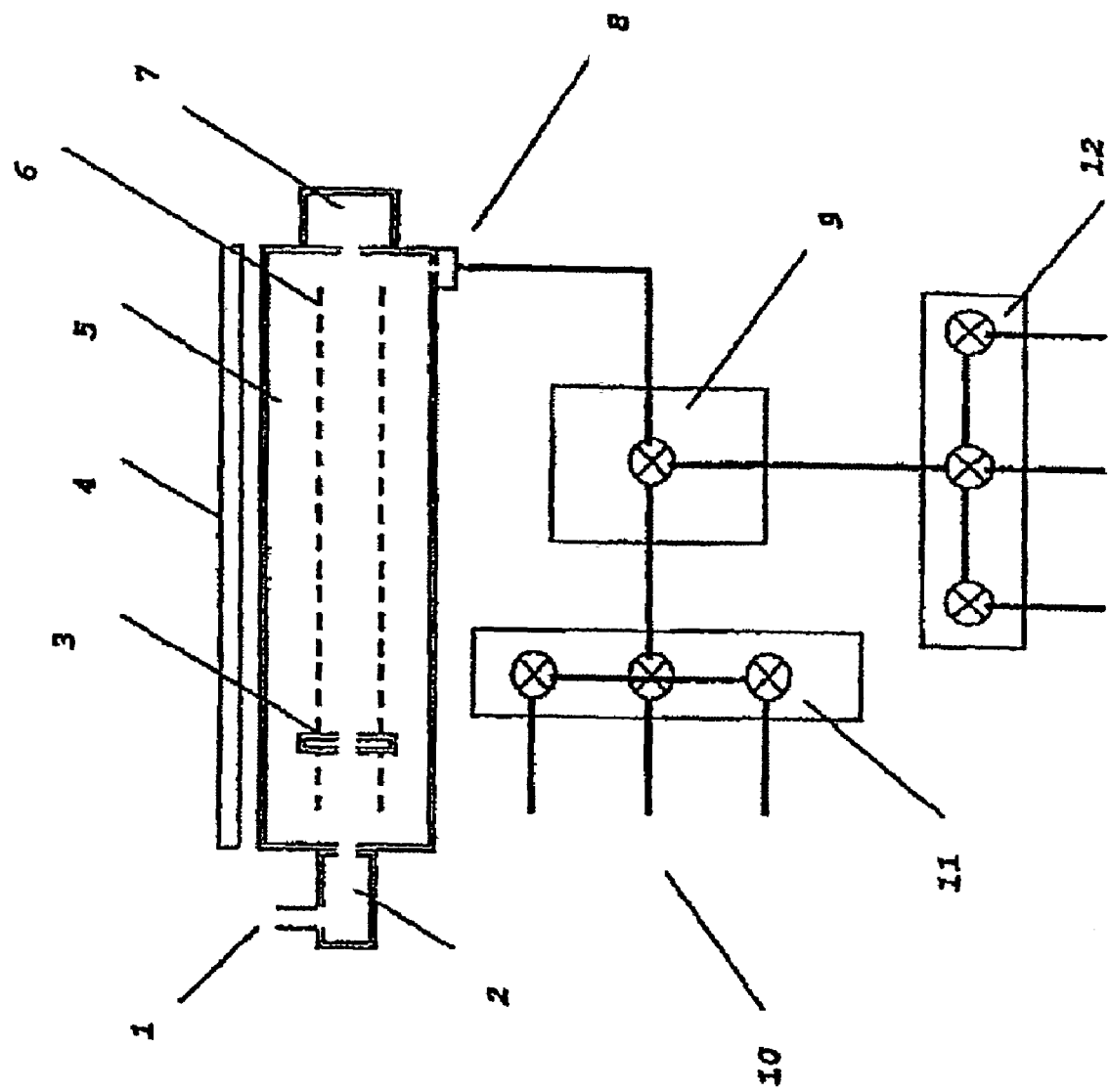
FIG. 1 shows a first exemplary embodiment of an ion mobility spectrometer according to the invention with an ion detector at the end of the drift tube.

The ion mobility spectrometer of FIG. 1 has a drift tube 5 to whose inlet is attached an ionization source 2 which has an orifice (sample inlet) 1 for the introduction of the sample. The sample may be supplied in solid, liquid or gaseous form to the sample inlet 1.

The drift tube 5 has, in a manner known per se, first electrodes 6 for the generation of an electrostatic field and second electrodes 3 for the generation of an electrical field which changes with time, by which the ion pulses can be generated. In the environment of the drift tube is also disposed a heating element 4, in order to enable the operation of the ion mobility spectrometer at higher temperatures. At the opposite end of the drift tube 5 to the ionization unit 2 is disposed an ion detector 7, for example a Faraday detector or an electron multiplier.

In the vicinity of the opposite end of the drift tube to the sample inlet 1, a further gas inlet 8 into the drift tube 5 is formed. This gas inlet 8 serves as the common gas inlet for the carrier gas and the collision gas. In a manner known per se, the carrier gas is thus admitted into the drift tube 5 in countercurrent to the analysis gas, in order to flush away neutral molecules which diffuse from the ion source into the drift tube. This countercurrent technique is applied especially in instruments which work at higher pressures.

Alternatively, the common gas inlet 8 may also be disposed at another point on the drift tube 5.

A gas supply system is connected to the gas inlet 8. This has a mixer 9 in which the carrier gas and the collision gas are mixed and fed into the drift tube 5 through a feed line which connects the mixer 9 and the gas inlet 8. The carrier gas and the collision gas are fed to the mixer 9 via feed lines.

The collision gas and the carrier gas may themselves each be mixed together from different components. The collision gas in particular, which is essential to the invention, is mixed in a collision gas inlet apparatus 10 and supplied to the mixer 9 in a common feed line.

The collision gas inlet apparatus 10 may, as shown, have three gas inlets, through which the, for example three, different types of collision gases may be supplied. In a collision gas mixer 11, the collision gases are then mixed.

In just this manner, different carrier gases can be supplied to a carrier gas inlet apparatus 12, mixed and supplied to the mixer 9 via a feed line.

Figure 2:
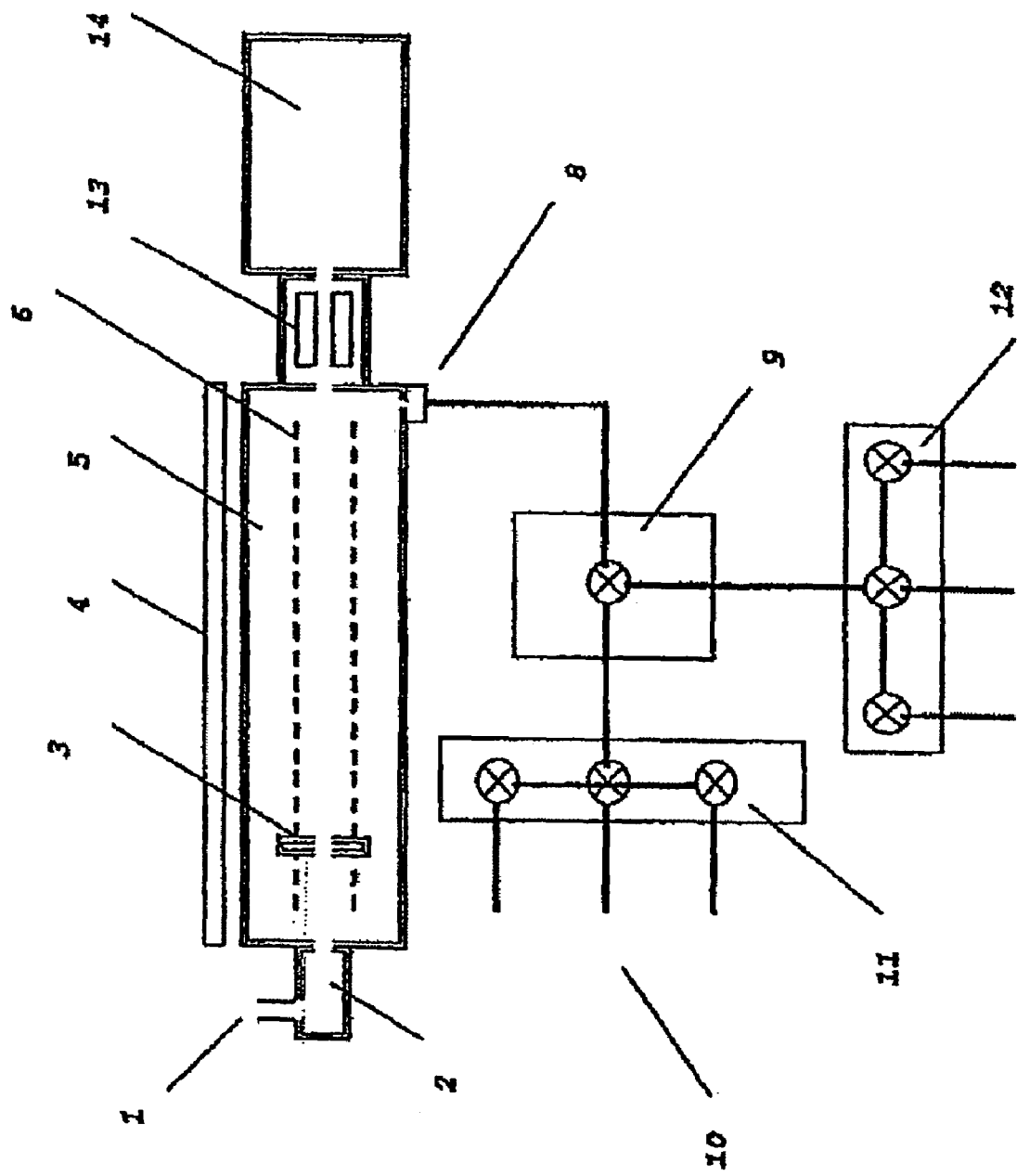
FIG. 2 shows a second exemplary embodiment of an ion mobility spectrometer according to the invention with a mass-selective detector at the end of the drift tube.

Instead of the ion detector 7 of FIG. 1, the embodiment of FIG. 2 has vacuum transfer optics 13 and a mass-selective detector 14 such as a mass spectrometer. In this detector, the enantiomeric ions are separated from other ions in accordance with the mass/charge ratio and detected. In addition to the mobility spectrum, a mass spectrum can thus be obtained in the sense of two-dimensional spectroscopy against time and mass/charge ratio of the sample.

Figure 3:
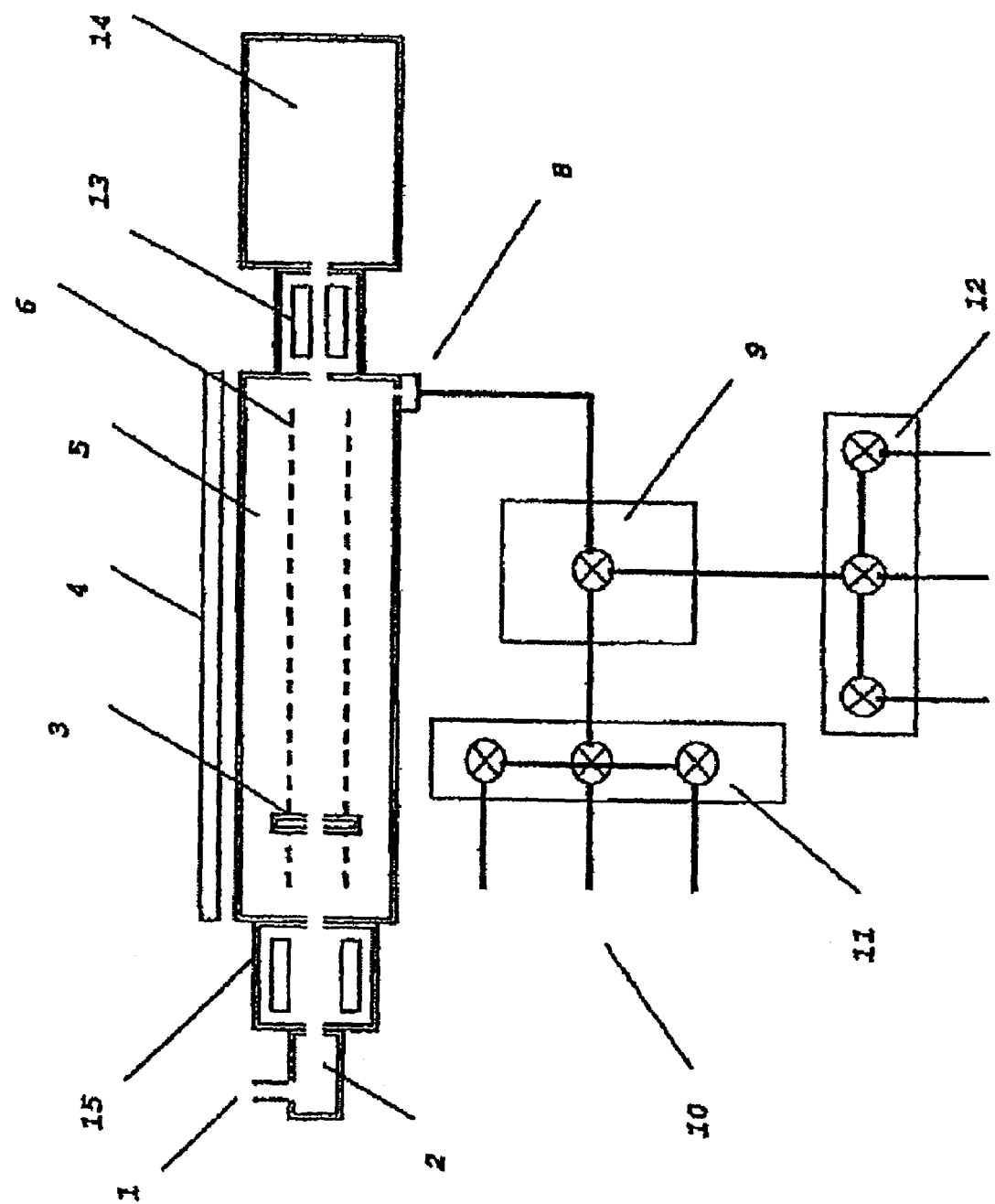
FIG. 3 shows a third exemplary embodiment of an ion mobility spectrometer according to the invention having a high-performance ionization source followed by vacuum transfer optics upstream of the inlet of the ion mobility spectrometer.

In the embodiment of FIG. 3, a high-vacuum ionization unit 2 is disposed upstream of the drift tube. After the ions have been generated, they are fed through vacuum transfer optics 15 into the high-pressure drift tube 5 of the ion mobility spectrometer, at whose end a mass-selective detector 14 is again disposed.

In all embodiments shown, a chromatographic or electrophoretic unit may additionally be provided upstream of the ion mobility spectrometer. For one substance to be analyzed, there is often a need to initially carry out a coarse separation of certain constituents before individual constituents are then fed with the purpose of fine separation to the ion mobility spectrometer for the performance of the process according to the invention. Such a coarse separation can be carried out with a chromatographic or electrophoretic unit. The outlet of such a chromatographic or electrophoretic unit may then be connected, for example, to the inlet of the ionization unit connected to the ion mobility spectrometer.

Measurements are introduced hereinbelow by which the effectiveness of the process according to the invention can be demonstrated.

In these measurements, the chiral substance fluoxetine is separated into its enantiomeric constituents in an ion mobility spectrometer. The measurements were carried out in an atmospheric-pressure ion mobility spectrometer with orthogonal time-of-flight mass spectrometer. The ions were introduced into the drift tube by an electrospray ionization source (ionization source 2 according to FIG. 2). The carrier gas or drift gas supplied to the inlet orifice 8 was nitrogen ($N_2$). Additionally supplied to it was S-2-butanol as an enantiomeric component of the chiral collision gas 2-butanol.

Figure 4:
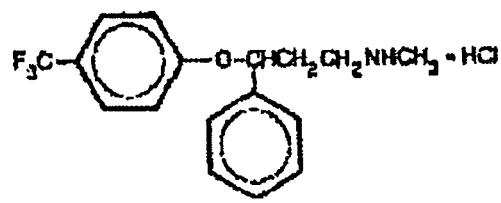
FIG. 4 shows the structural formula of the chiral compound fluoxetine:
(A) shows the ion mobility spectrum of a fluoxetine racemic mixture using a pure $N_2$ carrier gas;
(B) shows the same with doping of the carrier gas with 5 mol % of the S form of the chiral 2-butanol.
Figure 4:
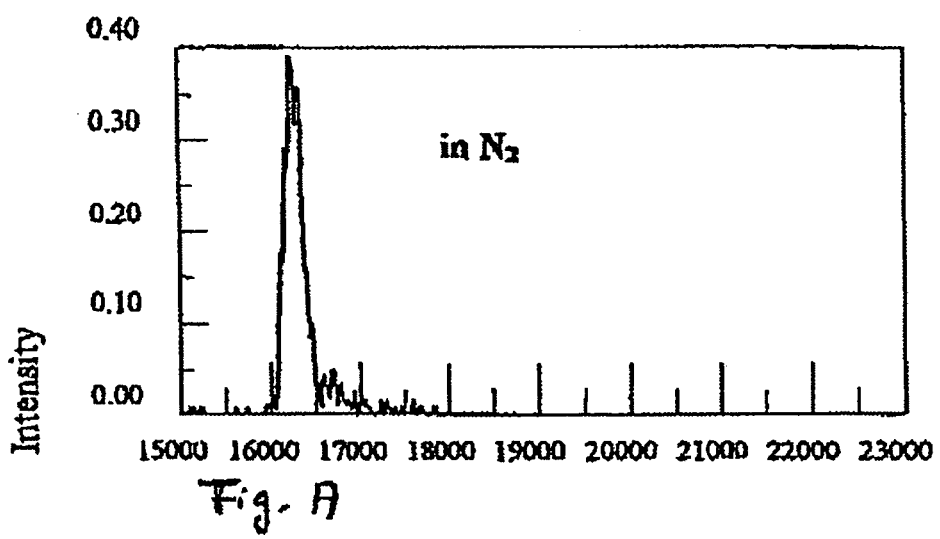
Figure 4:
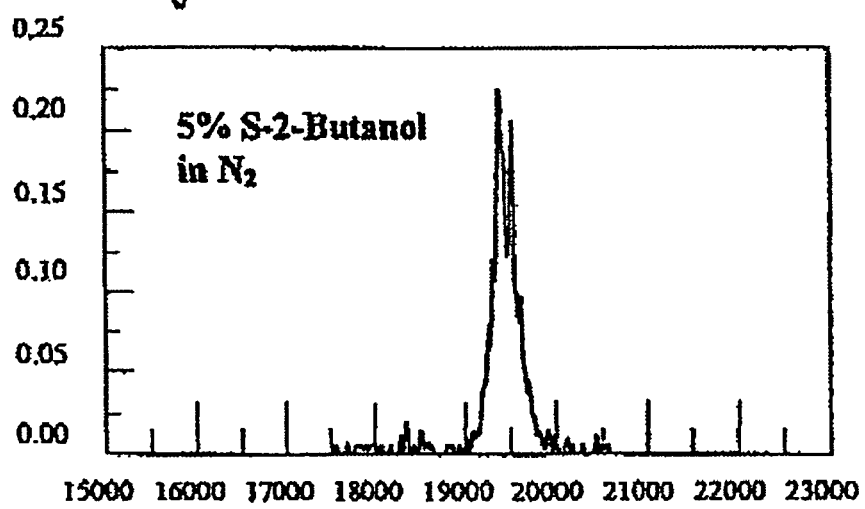

FIG. 4 shows first, in the upper section, the structural formula of the chiral compound fluoxetine. FIG. 4A shows the drift spectrum of a racemic mixture of fluoxetine without the addition by mixing of a selective collision gas. The drift time is approx. 16 ms. Since no selective stereochemical interaction is possible in the gas phase of the $N_2$ drift gas, only a single signal peak appears in the drift spectrum.

In contrast, FIG. 4B shows the drift spectrum of the same racemic mixture with the addition of 5% of the S form of 2-butanol as the selective collision gas. In the drift spectrum, two distinctly separate signals are registered for the two enantiomeric forms of fluoxetine. The drift time has shifted to longer times as a result of the change in the composition of the collision gas. This result thus clearly shows that 1. the collision molecule used, S-2-butanol, interacts with both enantiomeric components of the fluoxetine racemic mixture and prolongs the drift times, and
2. enters into interactions of different strengths with the two enantiomeric components, so that the mobilities of both components assume different values in the ion mobility spectrometer.

As already mentioned, the present invention is applicable in principle also to the separation of nonchiral components present in a sample. If, for example, two proteins having very similar drift times are to be separated from each other in an ion mobility spectrometer, a suitable collision molecule can be selected which is known to have a significantly greater interactive cross section with one of the protein molecules than with the other protein.

What is claimed is:

1. A separation process of components present in a sample, comprising:
   the sample being supplied to an ion mobility spectrometer, and
   also supplied to the ion mobility spectrometer is at least one separating substance which comprises gaseous particles which selectively interact with the molecules of the components to be separated.

2. The separation process of claim 1, wherein the components to be separated are chiral components.

3. The separation process of claim 1 or 2, wherein the separating substance comprises collision molecules.

4. The separation process of claim 3, wherein the collision molecules comprise enantiomeric molecules.

5. The separation process of claim 1 or 2, wherein the separating substance comprises macroscopic particles, in particular macromolecules or nanoparticles.

6. The separation process of claim 1, wherein a carrier or drift gas is supplied to the ion mobility spectrometer.

7. The separation process of claim 6, wherein the percentage (molar) ratio of separating substance to carrier gas assumes a value between 0 and 100%.

8. The separation process of claim 6 or 7, wherein the carrier gas and the separating substance are mixed in a gas supply system, and
   supplied to a common gas inlet of the ion mobility spectrometer.

9. The separation process of claim 8, wherein
   the analysis medium is supplied to an analysis inlet disposed at one end of the ion mobility spectrometer, and
   the common gas inlet is disposed at the other end of the ion mobility spectrometer.

10. An ion mobility spectrometer for the separation of components present in an analysis medium, comprising
    a sample inlet, and
    a separating substance inlet to supply at least one separating substance which comprises particles which selectively interact with the molecules of the components to be separated.

11. The ion mobility spectrometer of claim 10, wherein the separating substance inlet is also the carrier gas inlet.

12. The ion mobility spectrometer of claim 10, wherein the separating substance inlet is not simultaneously the carrier gas inlet.

13. An apparatus for the separation of components present in a sample, comprising:
    an ion mobility spectrometer as recited in claim 10, and
    a gas supply system connected to the separating substance inlet.

14. The apparatus of claim 13, wherein
    the separating substance inlet is also the carrier gas inlet,
    the combined separating substance/carrier gas inlet is combined with a mixer, and
    in each case at least one supply line for a separating substance and a carrier gas opens into the mixer.

15. The apparatus of claim 13, wherein
    the separating substance inlet is not simultaneously the carrier gas inlet,
    the separating substance inlet is connected to a mixer, and
    a plurality of supply lines for at least one separating substance and/or gaseous particles opens into the mixer.

16. An apparatus for the separation of components present in a sample comprising:
    an ion mobility spectrometer as recited in claim 10, and
    a chromatographic or electrophoretic unit connected upstream of the ion mobility spectrometer.

17. An apparatus for the separation of components present in a sample comprising:
    an ion mobility spectrometer as recited in claim 10, and
    an ion detection unit connected downstream of the ion mobility spectrometer.

* * * * *